United States Patent [19]
Tarumi et al.

[11] Patent Number: 5,968,412
[45] Date of Patent: Oct. 19, 1999

[54] LIQUID-CRYSTALLINE MEDIUM

[75] Inventors: Kazuaki Tarumi, Seeheim; Brigitte Schuler, Grossostheim; Eike Poetsch, Mühltal, all of Germany

[73] Assignee: Merck Patent Gesellschaft MIT Berschrankter Haftung, Germany

[21] Appl. No.: 08/986,335

[22] Filed: Dec. 5, 1997

[30] Foreign Application Priority Data

Dec. 6, 1996 [DE] Germany .................. 196 50 635

[51] Int. Cl.$^6$ ................ C09K 19/30; C09K 19/12
[52] U.S. Cl. ................ 252/299.63; 252/299.66
[58] Field of Search ............. 252/299.63, 299.66

[56] References Cited

U.S. PATENT DOCUMENTS

| | | | |
|---|---|---|---|
| 4,877,548 | 10/1989 | Kitano et al. | 252/299.63 |
| 4,880,562 | 11/1989 | Kitano et al. | 252/299.63 |
| 5,183,587 | 2/1993 | Kitano et al. | 252/299.63 |
| 5,328,642 | 7/1994 | Rieger et al. | 252/299.63 |
| 5,364,556 | 11/1994 | Schadt et al. | 252/299.01 |
| 5,403,512 | 4/1995 | Bartmann et al. | 252/299.01 |
| 5,653,911 | 8/1997 | Kondo et al. | 252/299.01 |
| 5,720,899 | 2/1998 | Kondo et al. | 252/299.01 |
| 5,723,682 | 3/1998 | Poetsch et al. | 568/655 |

*Primary Examiner*—C. H. Kelly
*Attorney, Agent, or Firm*—Millen, White, Zelano & Branigan, P.C.

[57] ABSTRACT

Liquid-crystalline medium based on a mixture of polar compounds having positive dielectric anisotropy, characterized in that it comprises one or more compounds of the general formula I,

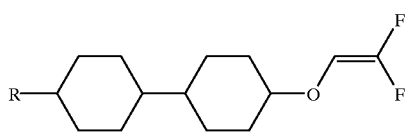

in which R is H, an alkyl or alkenyl radical having 1 to 15 carbon atoms which is unsubstituted by CN or CF$_3$ or at least monosubstituted by halogen, it also being possible for one or more CH$_2$ groups in these radicals to be replaced, in each case independently of one another, by —O—, —S—,

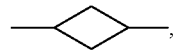

—CO—, —CO—O—, O—CO— or —O—CO—O— in such a way that O atoms are not linked directly to one another and additionally comprises one or more compounds selected from the group consisting of the general formulae II, III, IV, V and VI defined herein.

9 Claims, No Drawings

LIQUID-CRYSTALLINE MEDIUM

BACKGROUND OF THE INVENTION

The present invention relates to a liquid-crystalline medium, to the use thereof for electro-optical purposes, and to displays containing this medium.

Liquid crystals are used, in particular, as dielectrics in display devices, since the optical properties of such substances can be modified by an applied voltage. Electro-optical devices based on liquid crystals are extremely well known to the person skilled in the art and can be based on various effects. Examples of such devices are cells having dynamic scattering, DAP (deformation of aligned phases) cells, guest/host cells, TN (twisted nematic) cells, STM (supertwisted nematic) cells, SBE (superbirefringence effect) cells and OMI (optical mode interference) cells. The most common display devices are based on the Schadt-Helfrich effect and have a twisted nematic structure.

The liquid-crystal materials must have good chemical and thermal stability and good stability to electric fields and electromagnetic radiation. Furthermore, the liquid-crystal materials should have relatively low Viscosity and give short addressing times, low threshold voltages and high contrast in the cells.

Furthermore, they should have a suitable mesophase, for example a nematic or cholesteric mesophase for the above-mentioned cells, at conventional operating temperatures, i.e., in the broadest possible range above and below room temperature. Since liquid crystals are generally used in the form of mixtures of a plurality of components, it is important that the components are readily miscible with one another. Further properties, such as the electrical conductivity, the dielectric anisotropy and the optical anisotropy, must satisfy different requirements depending on the cell type and area of application. For example, materials for cells having a twisted nematic structure should have positive dielectric anisotropy and low electrical conductivity.

For example, media of large positive dielectric anisotropy, broad nematic phases, relatively low birefringence, very high resistivity, good UV and temperature stability and low vapour pressure are desired for matrix liquid-crystal displays having integrated nonlinear elements for switching individual pixels (MLC displays).

Matrix liquid-crystal displays of this type are known. Examples of nonlinear elements which can be used for individual switching of individual pixels are active elements (i.e. transistors). This is then referred to as an "active matrix", and a differentiation can be made between two types:

1. MOS (metal oxide semiconductor) or other diodes on silicon wafers as substrate.
2. Thin-film transistors (TFTs) on a glass plate as substrate.

Use of monocrystalline silicon as the substrate material limits the display size, since even modular assembly of the various part-displays results in problems at the joints.

In the case of the more promising type 2, which is preferred, the electro-optical effect used is usually the TN effect. A differentiation is made between two technologies: TFTs comprising compound semiconductors, such as, for example, CdSe, or TFTs based on polycrystalline or amorphous silicon. Intensive work is being carried out worldwide on the latter technology.

The TFT matrix is applied to the inside of one glass plate of the display, whilst the other glass plate carries the transparent counterelectrode on the inside. Compared with the size of the pixel electrode, the TFT is very small and has virtually no adverse effect on the image. This technology can also be extended to fully colour-compatible image displays, where a mosaic of red, green and blue filters is arranged in such a way that each filter element is located opposite a switchable pixel.

The TFT displays usually operate as TN cells with crossed polarizers in transmission and are illuminated from the back.

The term MLC displays here covers any matrix display containing integrated nonlinear elements, i.e., in addition to the active matrix, also displays containing passive elements, such as varistors or diodes (MIM=metal-insulator-metal).

MLC displays of this type are particularly suitable for TV applications (for example pocket TV sets) or for high-information displays for computer applications (laptops) and in automobile or aircraft construction. In addition to problems with respect to the angle dependence of the contrast ad the response times, problems arise in MLC displays owing to inadequate resistivity of the liquid-crystal mixtures [TOGASHI, S., SEKIGUCHI, K., TANABE, H., YAMAMOTO, E., SORIMACHI, K., TAJIMA, E., WATANABE, H., SHIMIZU, H., Proc. Eurodisplay 84, September 1984: A 210–288 Matrix LCD Controlled by Double Stage Diode Rings, p. 141 ff, Paris; STROMER, M., Proc. Eurodisplay 84, September 1984: Design of Thin Film Transistors for Matrix Addressing of Television Liquid Crystal Displays, p. 145 ff, Paris]. With decreasing resistance, the contrast of an MLC display drops, and the problem of after-image elimination can occur. Since the resistivity of the liquid-crystal mixture generally drops over the life of an MLC display owing to interaction with the internal surfaces of the display, a high (initial) resistance is very important in order to obtain acceptable service lives. In particular in the case of low-voltage mixtures, it was hitherto not possible to achieve very high resistivities. It is furthermore important that the resistivity increases as little as possible with increasing temperature and after heating and/or exposure to UV radiation. Also particularly disadvantageous are the low-temperature properties of the mixtures from the prior art. It is required that crystallization and/or smectic phases do not occur, even at low temperatures, and that the temperature dependence of the viscosity is as low as possible. MLC displays of the prior art thus do not satisfy current requirements.

There thus continues to be a great demand for MLC displays having very high resistivity at the same time as a broad operating temperature range, short response times, even at low temperatures, and low threshold voltage which do not have these disadvantages or only do so to a reduced extent.

In the case of TX (Schadt-Helfrich) cells, media are desired which facilitate the following advantages in the cells:
 broadened nematic phase range (in particular down to low temperatures),
 switchability at extremely low temperatures (outdoor use, automobiles, avionics),
 increased stability on exposure to UV radiation (longer life).

The media available from the prior art do not enable these advantages to be achieved while simultaneously retaining the other parameters.

In the case of supertwisted cells (STN), media are desired which enable greater multiplexibility and/or lower threshold voltages and/or broader nematic phase ranges (in particular at low temperatures). To this end, a further extension of the parameter latitude available (clearing point, smectic-nematic transition or melting point, viscosity, dielectric quantities, elastic quantities) is urgently desired.
SUMMARY OF THE INVENTION The invention has the object of providing media, in particular for MLC, TN or STN displays of this type, which do not have the abovementioned disadvantages, or only do no to a reduced extent, and preferably at the same time have very high resistivities and low threshold voltages.

It has now been found that this object can be achieved when novel media are used in displays.

The invention thus relates to a liquid-crystal-line medium based on a mixture of polar compounds having positive dielectric anisotropy, characterized in that it comprises one or more compounds of the general formula I,

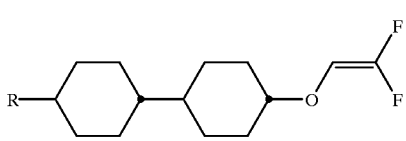

in which
R is H, an alkyl or alkenyl radical having 1 to 15 carbon atoms which is unsubstituted, monosubstituted by CM or CF$_3$ or at least monosubstituted by halogen, it also being possible for one or more CH$_2$ groups in these radicals to be replaced, in each case independently of one another, by —O—, —S—,

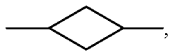

—CO—, —CO—O—, —O—CO— or —O—CO—O— in such a way that O atoms are not linked directly to one another.

The compounds of the formula I have a broad range of applications. Depend an the choice of substituents, these compounds can serve as base materials from which liquid-crystalline media are predominantly cased; however, compounds of the formula I can also be added to liquid-crystalline base materials from other classes of compound in order, for example, to modify the dielectric and/or optical anisotropy of a dielectric of this type and/or to optimize its threshold voltage and/or its viscosity.

In the pure state, the compounds of the formula I are colorless and form liquid-crystalline mesophases in a temperature range which is favorably located for electro-optical use. They are stable chemically, thermally and to light.

If R in the compounds of the formula I is an alkyl radical and/or an alkoxy radical, this can be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy. Furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy are also suitable.

Oxaalkyl is preferably straight-chain 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If R is an alkyl radical in which one CH$_2$ group has been replaced by —CH=CH—, this can be straight-chain or branched. It is preferably straight-chain and has 2 to 10 carbon atoms. Accordingly, it is in particular vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -9- or -9-enyl.

If R is an alkyl radical in which one CH$_2$ group has been replaced by —O— and one has been replaced by —CO—, these are preferably adjacent. These thus contain one acyloxy group —CO—O— or one oxycabonyl group —O—CO—. Those are preferably straight-chain and have 2 to 6 carbon atoms.

Accordingly, they are in particular acetoxy, propionyloxy, butyryloxy, pentanoylozy, hexanoyloxy, acetoxymethyl, propionyloxymethyl, butyryloxymethyl, pentanoyloxymethyl, 2-acetoxyethyl, 2-propionyloxy-ethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl) ethyl, 2-(ethoxycarbonyl) ethyl, 2-(propoxycarbonyl)ethyl, 3-(methoxycarbonyl) propyl, 3-(ethoxycarbonyl)propyl or 4-(methoxycarbonyl) butyl.

If R is an alkyl radical in which one CH$_2$ group has been replaced by unsubstituted or substituted —CH=CH— and an adjacent CH$_2$ group has been replaced by CO or CO—O or O—CO, this can be straight-chain or branched. It is preferably straight-chain and has 4 to 13 carbon atoms. Accordingly, it is in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl and 9-methacryloyloxynonyl.

If R is an alkyl or alkenyl radical which is monosubstituted by CN or CF$_3$, this radical is preferably straight-chain. The substitution by CM or CF$_3$ is in any desired position.

If R is an alkyl or alkenyl radical which is at least monosubstituted by halogen, this radical is preferably straight-chain and halogen is preferably F or Cl. In the case of multiple substitution, halogen is preferably F. The resultant radicals also include perfluorinated radicals. In the case of monosubstitution, the fluorine or chlorine substituent can be in any desired position, but preferably in the ω-position.

Compounds of the formula I which contain wing groups R which are suitable for polyaddition reactions are suitable for the preparation of liquid-crystalline polyaddition products.

Compounds of the formula I containing branched wing groups R may occasionally be of importance due to better solubility in the customary liquid-crystalline base materials, but in particular as chiral dopes if they are optically active. Smectic compounds of this type are suitable as components for ferroelectric materials.

Compounds of the formula I having S$_A$ phases are suitable, for example, for thermally addressed displays.

Branched groups of this type generally contain not more than one chain branch. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2methylpentoxy, 3-methylpentoxy, 2-ethylhexoxy, 1-methylhexoxy and 1-methylheptoxy.

If R is an alkyl radical in which two or more $CH_2$ groups have been replaced by —O— and/or —CO—O—, this may be straight-chain or branched. It is preferably branched and has 3 to 12 carbon atoms. Accordingly, it is, in particular, biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bis(methoxycarbonyl)ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)octyl, bis(ethoxycarbonyl)methyl, 2,2-bis(ethoxycarbonyl)ethyl, 3,3-bis(ethoxycarbonyl)propyl, 4,4-bis(ethoxycarbonyl)butyl and 5,5-bis(ethoxycarbonyl)hexyl.

The compounds of the formula I are prepared by methods known, per se, as described in the literature (for example in the standard works, such as Houbon-Weyl, Methoden der Organischen Chemie, Georg-Thieme-Verlag, Stuttgart), to be precise under reaction conditions which are known and suitable for said reactions. Use can also be made here of variants which are known, per se, but which are not mentioned here in greater detail.

The novel compounds can be prepared, for example, as follows:

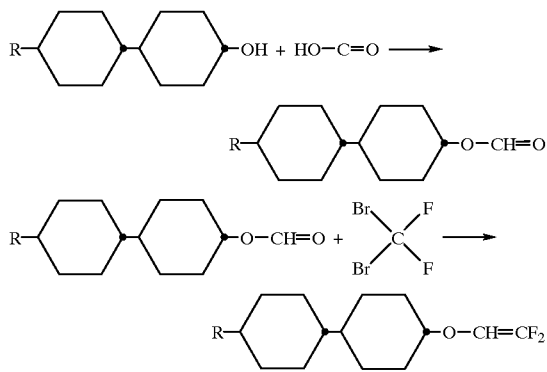

The invention also relates to electro-optical displays (in particular, STN or MLC displays having two plane-parallel outer plates which, together with a frame, form a cell, integrated nonlinear elements for switching individual pixels on the outer plates, and a nematic liquid-crystal mixture of positive dielectric anisotropy and high resistivity located in the call) which contain media of this type, and to the use of these media for electro-optical purposes.

The liquid-crystal mixtures, according to the invention, facilitate a significant broadening of the parameter latitude available.

The achievable combinations of clearing point, viscosity at low temperature, thermal and UV stability and dielectric anisotropy are far superior to previous materials from the prior art.

The requirement for a high clearing point, a nematic phase at low temperature and a high $\Delta\epsilon$ was previously only achievable to an unsatisfactory extent. Although systems such as, for example, ZLI-3119 have a comparable clearing point and comparatively favorable viscosities, they have, however, a $\Delta\epsilon$ of only +3.

Other mixture systems have comparable viscosities and values of $\Delta\epsilon$, but only have clearing points in the region of 60° C.

The liquid-crystal mixtures according to the invention make it possible to achieve clearing points of above 80°, preferably above 85°, particularly preferably above 90° C., and simultaneously dielectric anisotropy values $\Delta\epsilon \geq 5$, preferably $\geq 7$, and a high value for the resistivity while retaining the nematic phase down to −20° C. and preferably down to −30° C., particularly preferably down to −40° C., which allows excellent STN and MLC displays to be achieved. In particular, the mixtures are characterized by low operating voltages. The TN thresholds are below 2.0 V, preferably below 1.8 V, particularly preferably <1.6 V.

It goes without saying that a suitable choice of the components of the mixtures according to the invention also allows higher clearing points (for example above 110°) to be achieved at higher threshold voltages or lower clearing points to be achieved at lower threshold voltages while retaining the other advantageous properties. It is likewise possible to obtain mixtures of relatively high $\Delta\epsilon$ and thus relatively low thresholds if the viscosities are increased by a correspondingly small amount. The MLC displays according to the invention preferably operate in the first transmission minimum of Gooch and Tarry [C. E. Gooch and R. A. Tarry, Electron. Lett. 10, 2–4, 1974; C. H. Gooch and S. A. Tarry, Appl. Phys., Vol. 8, 1575–1584, 1975]; in this case, a lower dielectric anisotropy in the second minimum is sufficient in addition to particularly favorable electro-optical properties, such as, for example, high gradient of the characteristic line and low angle dependency of the contrast (German Patent 30 22 818) at the name threshold voltage as in an analogous display. This allows significantly higher resistivities to be achieved in the first minimum using the mixtures according to the invention than using mixtures containing cyano compounds. A person skilled in the art can use simple routine methods to produce the birefringence necessary for a prespecified layer thickness of the MLC display by a suitable choice of the individual components and their proportions by weight.

The rotational viscosity at 20° C. is preferably <150 mPa.s, particularly preferably <130 mPa.s. The nematic phase range is preferably at least 90°, in particular at least 100°. This range preferably extends at least from −20° to +80°.

Measurements of the "capacity holding ratio" (HR) [S. Matsumoto at al., Liquid Crystals 5, 1320 (1989); K. Kiwa et al., Proc. SID Conference, San Francisco, June 1984, p. 304 (1984): G. Weber et al., Licuid Crystals 5, 1381 (1989)] have shown that mixtures according to the invention comprising compounds of the formula I exhibit a considerably smaller decrease in the HR with increasing temperature than do analogous mixtures in which the compounds of the formula I are replaced by cyanophenylcyclohexanes of the formula

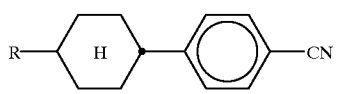

or esters of the formula

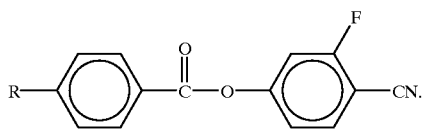

In addition, it has been found that novel mixtures comprising compounds of the formula I have a higher clearing point and a higher $\Delta\epsilon$ than analagous mixtures comprising cyanophenylcyclohexanes of the above formula. Compared with the last-mentioned mixtures, the novel mixtures also have a lower $\Delta n$, which is advantageous for many applications.

The UV stability of the mixtures according to the invention is also considerably better, i.e., they exhibit a significantly smaller decrease in the HR on exposure to UV radiation.

The media according to the invention are preferably based on a plurality (preferably two or more) of compounds of the formula I, i.e., the proportion of these compounds is 5–95%, preferably 10–60% and particularly preferably in the range 13–50%.

The individual compounds of the formulae I to XII and their sub-formulae which can be used in the media according to the invention are either known or can be prepared analogously to the known compounds.

Preferred embodiments are indicated below:

The compound of the formula I is a difluorovinyl ether of the formula Ia

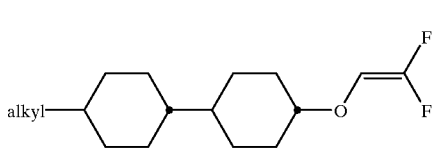

in which alkyl is an alkyl radical having 1–8 carbon atoms;

Medium additionally comprises one or move compounds selected from the group consisting of the general formulae II to VI:

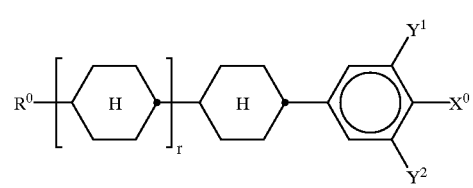

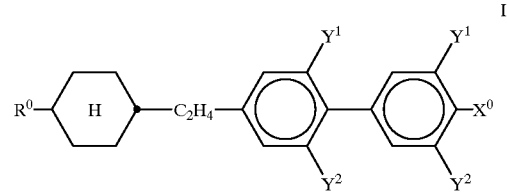

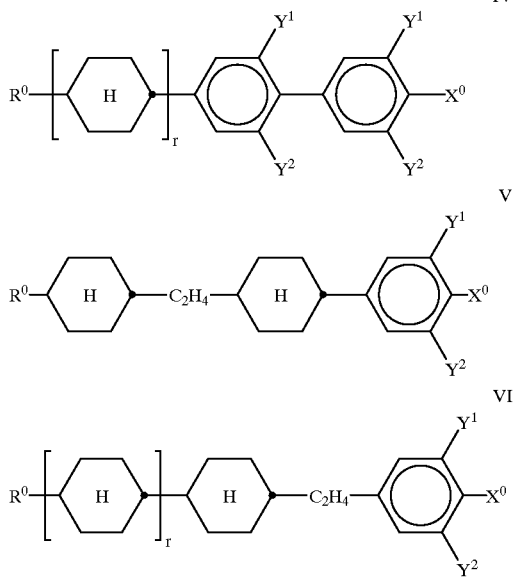

in which the individual radicals have the following meanings:

$R^0$: n-alkyl, oxaalkyl, fluoroalkyl or alkenyl, in each case having up to 9 carbon atoms, $X^0$: F, Cl, halogenated alkyl, alkenyl or alkoxy having 1 to 6 carbon atoms, $Y^1$ and $Y^2$: in each case, independently of one another, H or F, r: 0 or 1.

The compound of the formula IV is preferably

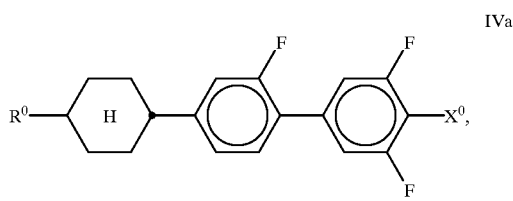

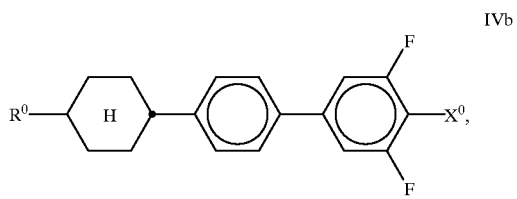

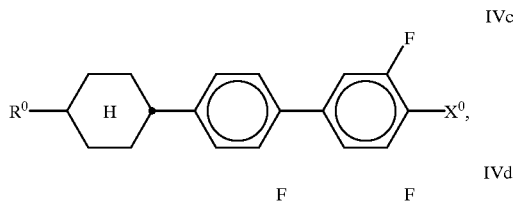

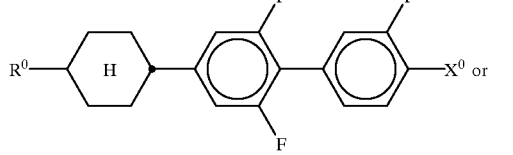

-continued

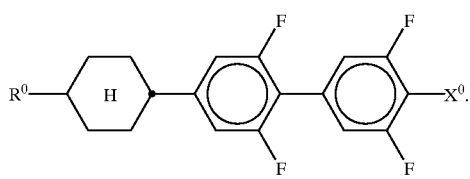
IVe

Medium additionally one or more compounds selected from the group consisting of the general formulae VII to XII:

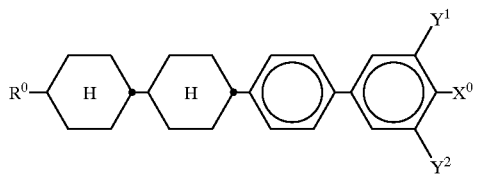
VII

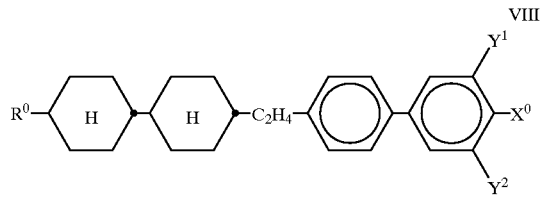
VIII

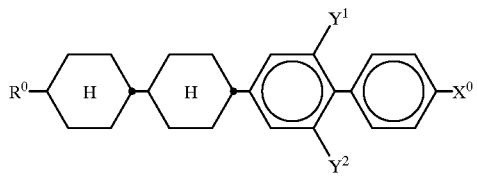
IX

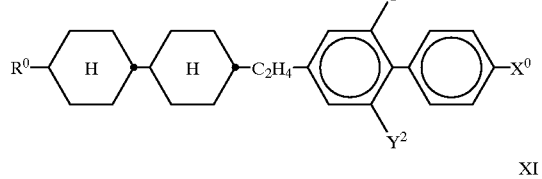
X

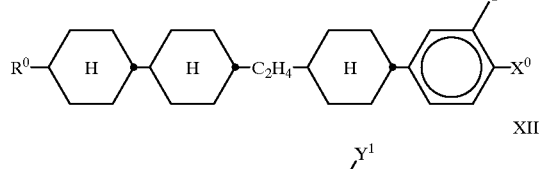
XI

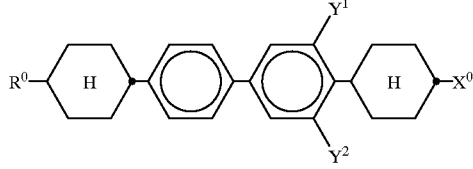
XII in which $R^0$, $X^0$, $Y^1$, and $Y^2$ are each, independently of one another, as defined in Claim 2, preferably F, Cl, $CF_3$, $OCF_3$, $OCHF_2$, alkyl, oxaalkyl, fluoroalkyl or alkenyl, in each case having up to 6 carbon atoms.

The medium additionally comprises one or more compounds of the formula IIa:

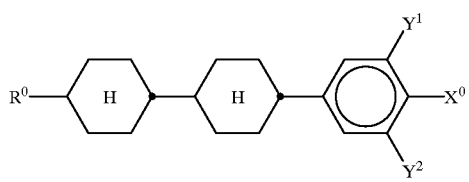
IIa

The proportion of compounds of the formulae I to VI together is at leant 50% by weight in the total mixture;

The proportion of compounds of the formula I is from 10 to 50% by weight in the total mixture;

The proportion of compounds of the formulae II to VI is from 30 to 70% by weight in the total mixture

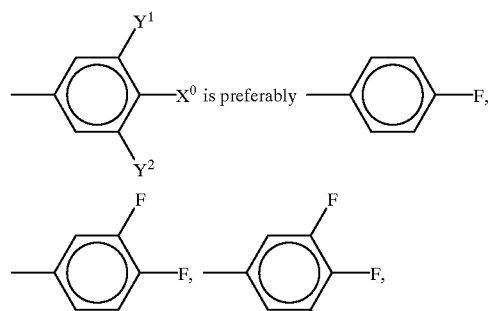

$X^0$ is preferably

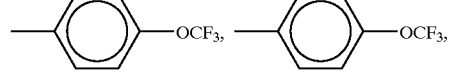

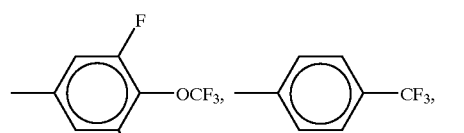

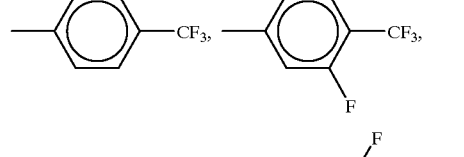

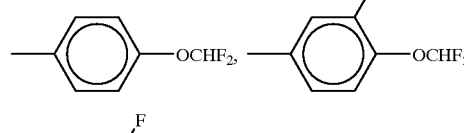

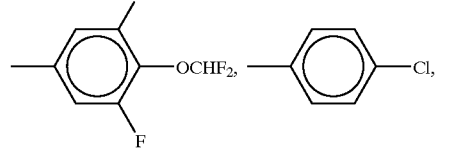

-continued

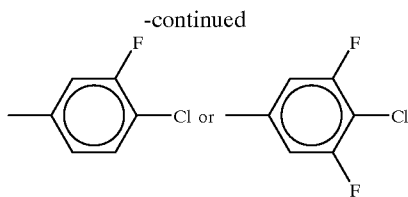

The medium comprises compounds of the formulae II, III, IV, V or VI $R^0$ is straight-chain alkyl or alkenyl having 2 to 7 carbon atoms The medium essentially consists of compounds of the formulae I to VI The medium comprises further compounds, preferably selected from the following group consisting of the general formulae XIII to XVI:

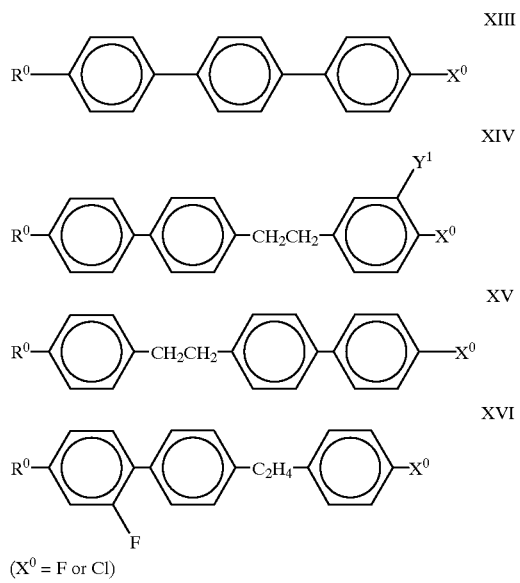

in which $R^0$ and $X^0$ are as defined above, and the 1,4-phenylene rings may be substituted by CN, chlorine or fluorine. The 1,4-phenylene ring are preferably monosubstituted or polysubstituted by fluorine atoms. The I: (II+III+IV+V+VI) weight ratio is preferably from 1:10 to 10:1.

Medium essentially consists of compounds selected from the group consisting of the general formulae I to XII.

It has been found that even a relatively small proportion of compounds of the formula I mixed with conventional liquid-crystal materials, but in particular with one or more compounds of the formula II, III, IV, V and/or VI, results in a significant reduction in the threshold voltage and in low birefringence values, and at the same time broad nematic phases with low smectic-nematic transition temperatures are observed, thus improving the shelf life. Particular preference is given to mixtures which, in addition to one or more compounds of the formula I, comprises one or more compounds of the formula IV, in particular compounds of the formula IVa in which $X^0$ is F or $OCF_3$. The compounds of the formulae I to VI are colorless, stable and readily miscible with one another and with other liquid-crystal materials.

The term "alkyl" covers straight-chain and branched alkyl groups having 1–7 carbon atoms, in particular the straight-chain groups methyl, ethyl, propyl, butyl, pentyl, hexyl and heptyl. Groups having 2–5 carbon atoms are generally preferred.

The term "alkenyl" covers straight-chain and branched alkenyl groups having 2–7 carbon atoms, in particular the straight-chain groups. In particular, alkenyl groups are $C_2$–$C_7$-1E-alkenyl, $C_4$–$C_7$-3E-alkenyl, $C_5$–$C_7$-4-alkenyl, $C_6$–$C_7$-5-alkenyl and $C_7$-6-alkenyl, in particular $C_2$–$C_7$-1E-alkenyl, $C_4$–$C_7$-3E-alkenyl and $C_5$–$C_7$-4-alkenyl. Examples of preferred alkenyl groups are vinyl, 1E-propenyl, 1E-butenyl, 1E-pentenyl, 1E-hexenyl, 1E-heptenyl, 3-butenyl, 3pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "fluoroalkyl" preferably covers straight-chain groups containing terminal fluorine, i. e. fluoromethyl, 2-fluoroethyl, 3-fluoropropyl, 4-fluorobutyl, 5-fluoropentyl, 6-fluorohexyl and 7-fluoroheptyl. However, other positions of the fluorine are not excluded.

The term "oxaalkyl" preferably covers straight-chain radicals of the formula $C_nH_{2n+1}$—O—$(CH_2)_m$, in which n and m are each, independently of one another, from 1 to 6. n is preferably 1 and m is preferably from 1 to 6.

Through a suitable choice of the meanings of $R^0$ and $X^0$, the addressing times, the threshold voltage, the gradient of the transmission characteristic lines, etc., can be modified as desired. For example, 1E-alkenyl radical, 3E-alkenyl radicals, 2E-alkenyloxy radicals and the like generally give shorter addressing times, improved nematic tendencies and a higher ratio between the elastic constants $k_{33}$ (bend) and $k_{11}$ (splay) compared with alkyl and alkoxy radicals. 4-Alkenyl radicals, 3-alkenyl radicals and the like generally give lower threshold voltages and lower values of $k_{33}/k_{11}$ compared with alkyl and alkoxy radicals.

A —$CH_2CH_2$— group generally results in higher values of $k_{33}/k_{11}$ compared with a simple covalent bond. Higher values of $k_{33}/k_{11}$ facilitate, for example, flatter transmission characteristic lines in TN cells with a 90° twist (for achieving grey tones) and steeper transmission characteristic lines in STN, SBE and OMI cells (greater multiplexibility), and vice versa.

The optimum mixing ratio of the compounds of the formulae I and II+III+IV+V+VI depends substantially on the desired properties, on the choice of the components of the formulae I, II, III, IV, V and/or VI and on the choice of any other components which may be present. Suitable mixing ratios within the abovementioned range can easily be determined from case to case.

The total amount of compounds of the formulae I to XII in the mixtures according to the invention is not crucial. The mixtures may therefore contain one or more further components in order to optimize various properties. However, the effect observed on the addressing times and the threshold voltage is generally greater the higher the total concentration of compounds of the formulae X to XII.

In a particularly preferred embodiment, the media according to the invention comprises compounds of the formulae II to VI (preferably II, III and/or IV, in particular IVa) in which $X^0$ is F, $OCF_3$, $OCHF_2$, $OCR$=$CF_2$, $OCF$=$CF_2$ at $OCF_2$—$CF_2H$. A favorable synergistic effect with the compounds of the formula results in particularly advantageous properties. In particular, mixtures comprising compounds of the formula I and of the formula IVa are distinguished by their low threshold voltages.

The construction of the MLC display according to the invention from polarizers, electrode base plates and electrodes with surface treatment corresponds to the construction which is conventional for displays of this type. The term conventional construction here is broadly drawn and also covers all derivatives and modifications of the MLC display, in particular also matrix display elements based on poly-Si TFTs or MIMs.

An essential difference between the displays according to the invention and those customary hitherto based on the twisted nematic cell is, however, the choice of the liquid-crystal parameters in the liquid-crystal layer.

The liquid-crystal mixtures which can be used according to the invention are prepared in a manner which is conventional, per se. In general, the desired amount of the component used in the lesser amount is dissolved in the components making up the principal constituent, expediently at elevated temperature. It is also possible to mix solutions of the components in an organic solvent, for example in acetone, chloroform or methanol, and, after thorough mixing, to remove the solvent again, for example by distillation.

The dielectrics may also contain other additives known to those skilled in the art and described in the literature. For example, 0–15% of pleochroic dyes or chiral dopes can be added.

C denotes a crystalline phase, S a smectic phase, $S_C$ a smectic C phase, N a nematic phase and I the isotropic phase.

$V_{10}$ denotes the voltage for 10% transmission (view angle perpendicular to the plate surface). $t_{on}$ denotes the switch-on time and $t_{off}$ the switch-off time at an operating voltage corresponding to 2.5 tires the value of $V_{10}$. $\Delta n$ denotes the optical anisotropy and $n_o$ the refractive index. $\Delta \epsilon$ denotes the dielectric anisotropy ($\Delta \epsilon = \epsilon_\| - \epsilon_\perp$, where $\epsilon_\|$ is the dielectric constant parallel to the longitudinal molecular axes and $\epsilon_\perp$ is the dielectric constant perpendicular thereto). The electro-optical data were measured in a TN cell at the 1st minimum (i.e., at a d·$\Delta$n value of 0.5) at 20° C., unless expressly stated otherwise. The optical data were measured at 20° C., unless expressly stated otherwise.

In the present application and in the examples below, the structures of the liquid-crystal compounds are indicated by acronyms, with the transformation into chemical formulae taking place in accordance with Tables A and B below. All radicals $C_nH_{2n+1}$ and $C_mH_{2m+1}$ are straight-chain alkyl radicals containing n or m carbon atoms, respectively. The coding in Table B is self-evident. In Table A, only the acronym for the base structure is given. In individual cases, the acronym for the base structure is followed, separated by a hyphen, by a code for the substituents $R^1$, $R^2$, $L^1$ and $L^2$:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nF.F.F | $C_nH_{2n+1}$ | F | F | F |
| nCF$_3$ | $C_nH_{2n+1}$ | CF$_3$ | H | H |
| nOCF$_3$ | $C_nH_{2n+1}$ | OCF$_3$ | H | H |
| nOCF$_2$ | $C_nH_{2n+1}$ | OCHF$_2$ | H | H |
| nS | $C_nH_{2n+1}$ | NCS | H | H |
| rVsN | $C_rH_{2r+1}$—CH=CH—$C_sH_{2s}$— | CN | H | H |
| rEsN | $C_rH_{2r+1}$—O—$C_2H_{2s}$— | CN | H | H |
| nAm | $C_nH_{2n+1}$ | $COOC_mH_{2m+1}$ | H | H |
| nOCCF$_2$.F.F | $C_nH_{2n+1}$ | $OCH_2CF_2H$ | F | F |

Preferred mixture components are show in Tables A and B.

TABLE A

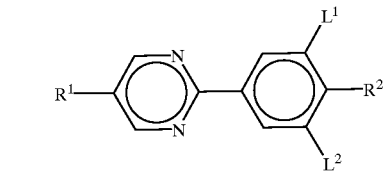

PYP

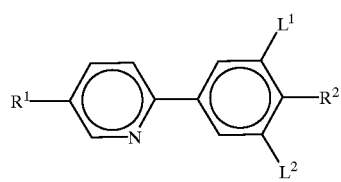

PYRP

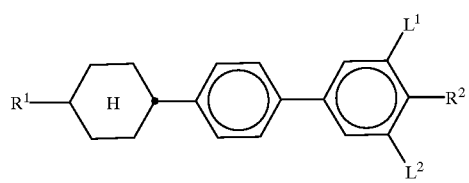

BCH

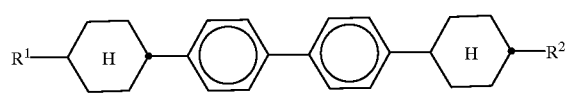

CBC

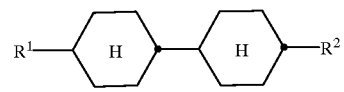

CCH

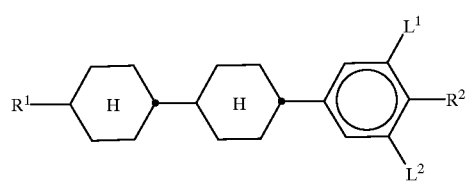

CCP

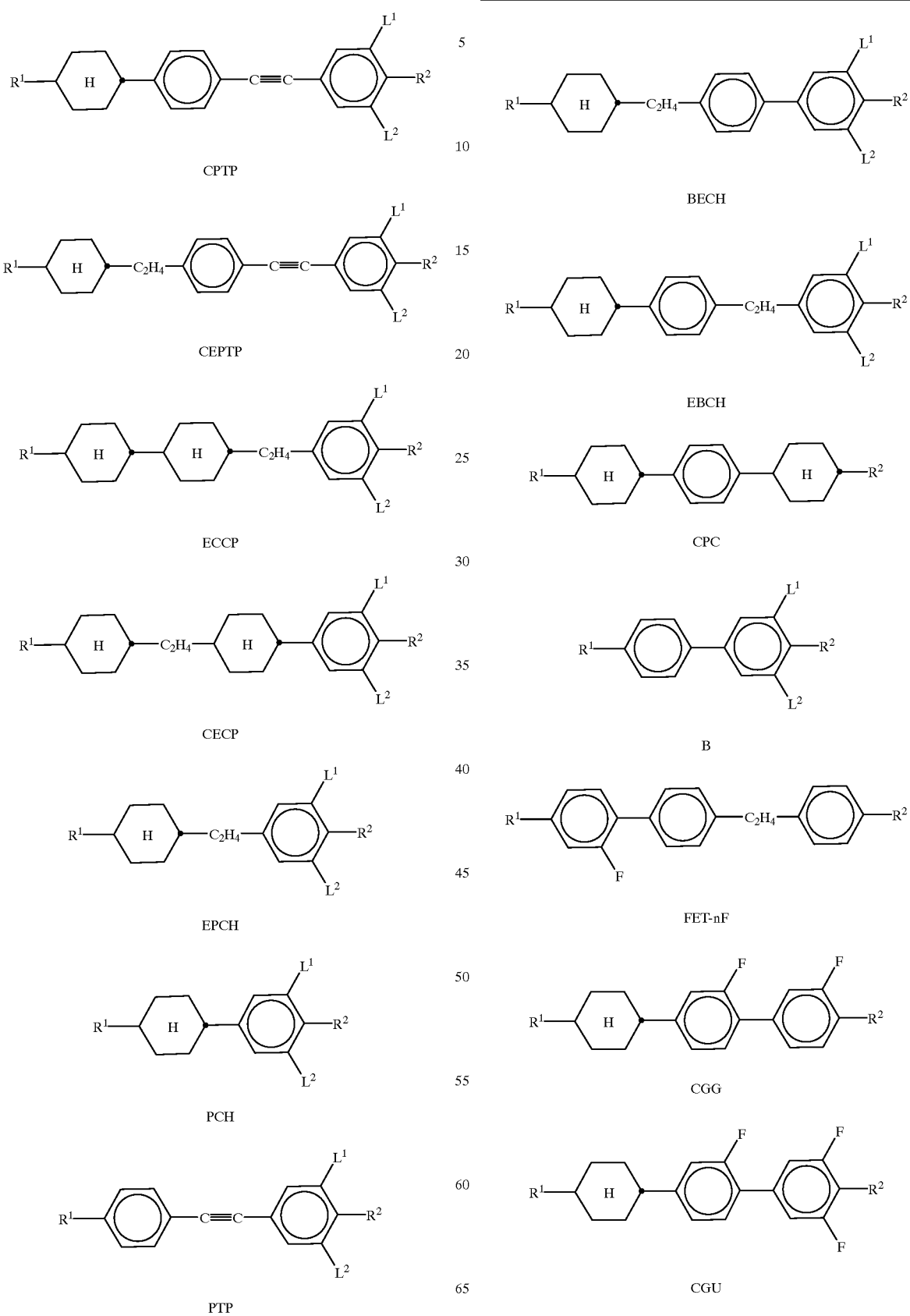

TABLE A-continued

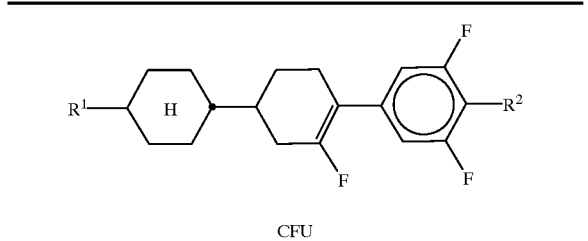

CFU

TABLE B

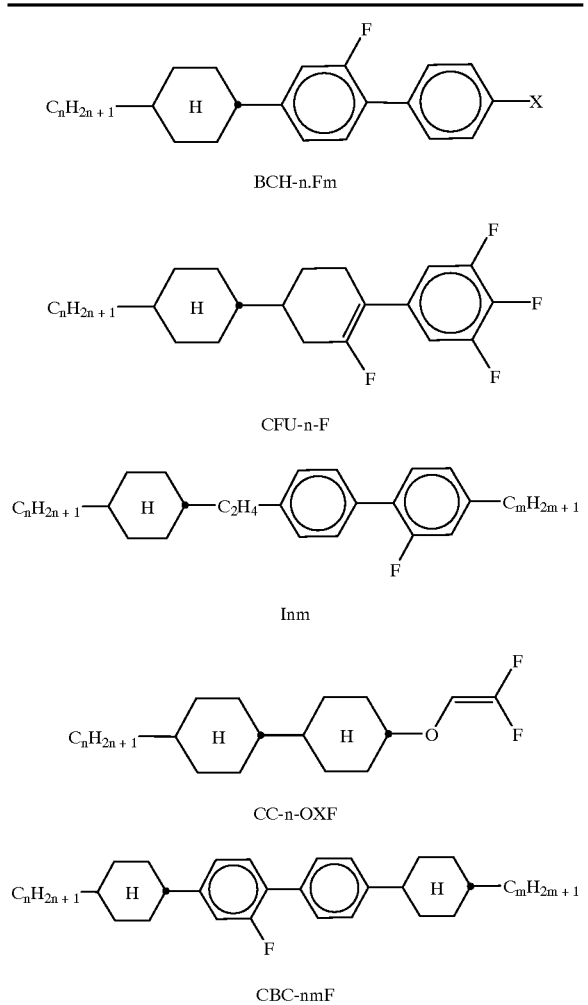

TABLE B-continued

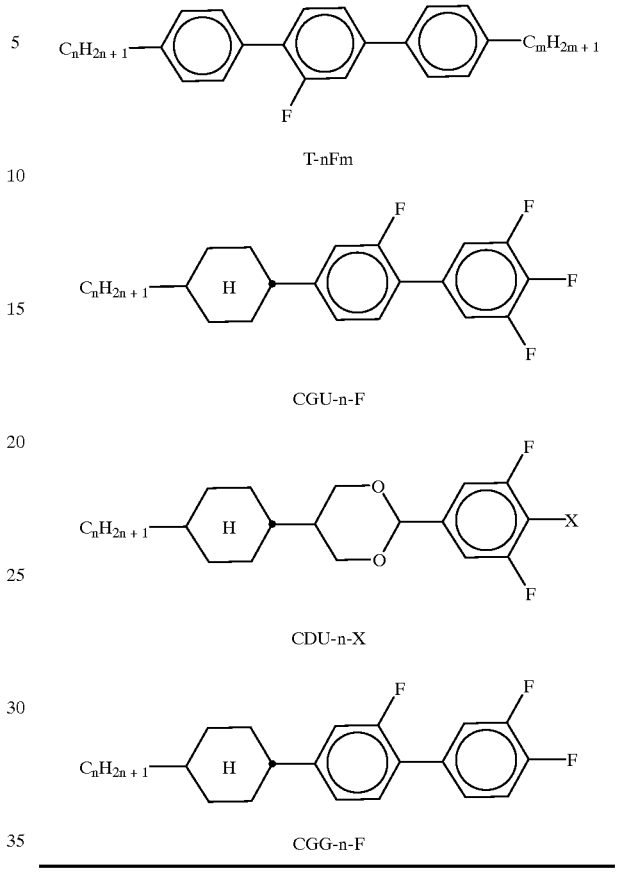

The entire disclosure of all applications, patents and publications, cited above and below, and of corresponding German application No. DE 19650635.2, filed Dec. 6, 1996 is hereby incorporated by reference.

The examples below are intended to illustrate the invention without representing a limitation. Above and below, percentages are percent by weight. All temperatures are given in degrees Celsius. m.p. denotes melting point, c.p.= clearing point. Furthermore, C=crystalline state, N=nematic phase, S=smectic phase and I=isotropic phase. The data between these symbols represent the transition temperatures. $\Delta n$ denotes the optical anisotropy (589 nm, ° C.), and the viscosity (mPa.sec) was determined at 20° C.

EXAMPLE

Example 1

| | | | |
|---|---|---|---|
| CC-3-OXF | 8.00 | Clearing point [°C.]: | +89 |
| CC-5-OXF | 10.00 | $\Delta N$ [589 nm, 20° C.]: | +0.0721 |
| CCN-34 | 5.00 | $\Delta \epsilon$ [1 kHz, 20° C.]: | — |
| CCN-35 | 5.00 | $V_{(10, 0, 20)}$ [V]: | 1.80 |
| CCP-20 CF3 | 8.00 | | |
| CCP-30 CF3 | 8.00 | | |
| CCP-40 CF3 | 8.00 | | |
| CCP-50 CF3 | 8.00 | | |
| CCP-2 F.F.F | 12.00 | | |
| CCP-3 F.F.F | 12.00 | | |
| CCP-5 F.F.F | 8.00 | | |
| ECCP-3 F.F | 8.00 | | |

-continued

| Example 2 | | | |
|---|---|---|---|
| CC-3-OXF | 5.00 | Clearing point [°C.]: | +92 |
| CC-5-OXF | 8.00 | Δn [589 nm, 20° C.]: | +0.0816 |
| CCP-20 CF3 | 8.00 | Δε [1 kHz, 20° C.]: | 7.7 |
| CCP-30 CF3 | 8.00 | $V_{(10, 0, 20)}$ [V]: | +1.53 |
| CCP-40 CF3 | 8.00 | | |
| CCP-50 CF3 | 8.00 | | |
| CCP-2 F.F.F | 12.00 | | |
| CCP-3 F.F.F | 12.00 | | |
| CCP-5 F.F.F | 8.00 | | |
| CGU-3-F | 6.00 | | |
| ECCP-3 F.F | 6.00 | | |
| CCP-30CF2.F.F | 11.00 | | |
| Example 3 | | | |
| CC-3-OXF | 8.00 | Clearing point [°C.]: | +86 |
| CC-5-OXF | 8.00 | Δn [589 nm, 20° C.]: | +0.0745 |
| CCH-34 | 5.00 | Δε [1 kHz, 20° C.]: | — |
| CCH-35 | 5.00 | $V_{(10, 0, 20)}$ [V]: | 1.62 |
| CCP-20 CF3 | 9.00 | | |
| CCP-30 CF3 | 8.00 | | |
| CCP-40 CF3 | 6.00 | | |
| CCP-50 CF3 | 8.00 | | |
| CCP-2 F.F.F | 11.00 | | |
| CCP-3 F.F.F | 12.00 | | |
| CCP-5 F.F.F | 7.00 | | |
| CGU-3-F | 4.00 | | |
| ECCP-3 F.F | 9.00 | | |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. Liquid-crystalline medium based on a mixture of polar compounds having positive dielectric anisotropy, characterized in that it comprises one or more compounds of the general formula I,

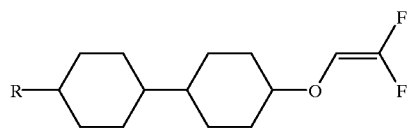

I in which

R is H, an alkyl or alkenyl radical having 1 to 15 carbon atoms which is unsubstituted, monosubstituted by CN or $CF_3$ or at least monosubstituted by halogen, it also being possible for one or more $CH_2$ groups in these radicals to be replaced, in each case independently of one another, by —O—, —S—,

,

—CO—, —CO—O—, —O—CO— or —O—CO—O— in such a way that O atoms are not linked directly to one another and additionally comprises one or more compounds selected from the group consisting of the general formulae II, III, IV, V and VI:

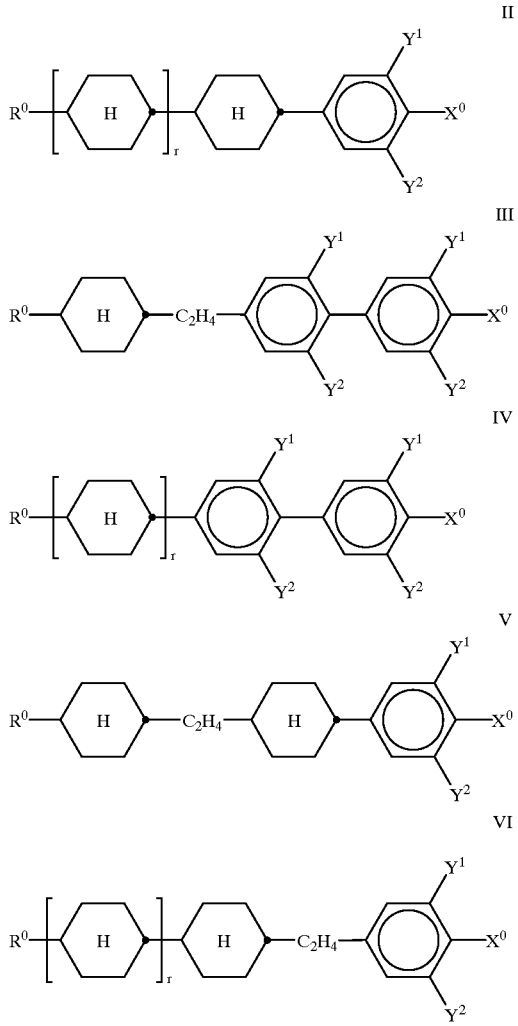

in which the individual radicals have the following meanings:

$R^0$: n-alkyl, oxaalkyl, fluoroalkyl or alkenyl, in each case having up to 7 carbons atoms, $X^0$ F, Cl, halogenated alkyl, alkenyl or alkoxy having 1 to 5 carbon atoms, $Y^1$ and $Y^2$: in each case, independently of one another, H or F, r: 0 or 1.

2. Medium according to claim 1, characterized in that the proportion of compounds of the formulae I to VI together is at least 50% by weight based on the weight of the total mixture.

3. Medium according to claim 1, characterized in that the proportion of compounds of the formula I is from 3 to 80% by weight based on the weight of the total mixture.

4. Medium according to claim 1, characterized in that the proportion of compounds of the formulae II to VI is from 20 to 80% by weight in the total mixture.

5. Medium according to one of claim 1, characterized in that R in the compound of the formula I is alkyl having 1 to 8 carbon atoms.

6. A method of using the liquid-crystalline medium according to claim 1 which comprises incorporating said liquid-crystalline medium in an electro-optical device.

7. Electro-optical liquid-crystal display containing a liquid-crystalline medium according to claim 1.

8. Liquid-crystalline medium based on a mixture of polar compounds having positive dielectric anisotropy, characterized in that it comprises one or more compounds of the general formula I

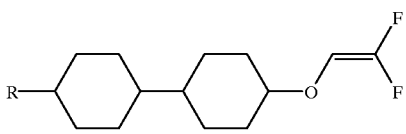

in which
R is H, an alkyl or alkenyl radical having 1 to 15 carbon atoms which is unsubstituted, monosubstituted by CN or $CF_3$ or at least monosubstituted by halogen, it also being possible for one or more $CH_2$ groups in these radicals to be replaced, in each case independently of one another, by —O—, —S—,

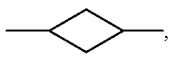

—CO—, —CO—O—, —O—CO— or —O—CO—O— in such a way that O atoms are not linked directly to one another and additionally comprises a compound of the formula IIa

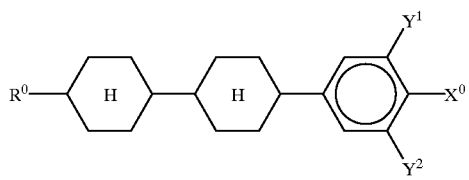

in which the individual radicals have the following meanings:

$R^0$: n-alkyl, oxaalkyl, fluoroalkyl or alkenyl, in each case having up to 7 carbon atoms, $X^0$ F, Cl, halogenated alkyl, alkenyl or alkoxy having 1 to 5 carbon atoms, $Y^1$ and $Y^2$: in each case, independently of one another, H or F.

9. Medium according to claim 8, characterized in that $X^0$ is F or $OCF_3$, and $Y^1$ and $Y^2$ are H or F.

* * * * *